(12) United States Patent
Keshava et al.

(10) Patent No.: US 10,304,006 B2
(45) Date of Patent: May 28, 2019

(54) METHOD FOR INTEGRATING AND FUSING HETEROGENEOUS DATA TYPES TO PERFORM PREDICTIVE ANALYSIS

(71) Applicant: The Charles Stark Draper Laboratory, Inc., Cambridge, MA (US)

(72) Inventors: Nirmal Keshava, Needham, MA (US); Laura Jane Mariano, Watertown, MA (US)

(73) Assignee: THE CHARLES STARK DRAPER LABORATORY, INC., Cambridge, MA (US)

( * ) Notice: Subject to any disclaimer, the term of this patent is extended or adjusted under 35 U.S.C. 154(b) by 917 days.

(21) Appl. No.: 14/183,018

(22) Filed: Feb. 18, 2014

(65) Prior Publication Data

US 2014/0236872 A1 Aug. 21, 2014

Related U.S. Application Data

(60) Provisional application No. 61/765,530, filed on Feb. 15, 2013.

(51) Int. Cl.
*G06F 15/18* (2006.01)
*G06N 20/00* (2019.01)
(Continued)

(52) U.S. Cl.
CPC ............. *G06N 20/00* (2019.01); *G06F 19/00* (2013.01); *G16H 50/20* (2018.01)

(58) Field of Classification Search
None
See application file for complete search history.

(56) References Cited

U.S. PATENT DOCUMENTS 6,216,119 B1 4/2001 Jannarone
6,569,403 B1 * 5/2003 Metz .................. A61K 51/0491
424/1.73

(Continued)

FOREIGN PATENT DOCUMENTS

WO 1998022885 A1 5/1998

OTHER PUBLICATIONS

"Prediction of Alzheimer's Disease Using the CSF AB42/AB40 Ratio in Patients with Mild Cognitive Impairment" Hansson et al, Dement Geriatr Cogn Disord 2007;23:316-320 DOI: 10.1159/000100926 Accepted: Jan. 18, 2007 Published online: Mar. 19, 2007.*

(Continued)

*Primary Examiner* — Luis A Sitiriche
(74) *Attorney, Agent, or Firm* — Lando & Anastasi, LLP

(57) ABSTRACT

A method and system for predicting the onset of a disease is provided. According to one example, the method includes receiving patient data including a first input sample of a first data type and a second input sample of a second data type, the first data type including discrete data and the second data type including continuous data, receiving a training data set including a first plurality of training samples of the first data type and a corresponding second plurality of training samples of the second data type, providing the first input sample and the first plurality of training samples to a first kernel function of a multiple kernel decision function, providing the second input sample and the second plurality of training samples to a second kernel function of the multiple kernel decision function, performing at least one calculation using the multiple kernel decision function to produce at least one result, and determining a probability of whether the patient data indicates that the patient will (Continued)

develop the disease based on the at least one result of the multiple kernel decision function.

18 Claims, 7 Drawing Sheets

(51) Int. Cl.
*G16H 50/20* (2018.01)
*G06F 19/00* (2018.01)

(56) References Cited

U.S. PATENT DOCUMENTS

| | | | |
|---|---|---|---|
| 6,647,377 B2 | 11/2003 | Jannarone | |
| 8,566,268 B2 | 10/2013 | Ebadollahi et al. | |
| 8,595,155 B2 | 11/2013 | Ide | |
| 9,087,294 B2* | 7/2015 | Kojaku | G06N 5/02 |
| 9,211,294 B2* | 12/2015 | Wischik | A61K 31/5415 |
| 2004/0103001 A1* | 5/2004 | Mazar | A61B 5/0002 |
| | | | 705/2 |
| 2004/0265919 A1* | 12/2004 | Vanderstichele | G01N 33/6896 |
| | | | 435/7.2 |
| 2009/0043795 A1* | 2/2009 | Kenedy | G06F 19/345 |
| | | | 707/999.101 |
| 2011/0257025 A1* | 10/2011 | Houtman | G01N 33/574 |
| | | | 506/9 |
| 2013/0097108 A1 | 4/2013 | Niculescu-Mizil et al. | |

OTHER PUBLICATIONS

Cortes, C. and V. Vapnik (1996). "Support-Vector Networks." Machine Learning 20(3): 273-297.

Hinrichs, C. V. Singh, et al. (2011). "Predictive markers for AD in a multi-modality framework: An analysis of MCI progression in the ADNI population." NeuroImage 55(2): 574-589.

Mika, S., G. Ratsch, et al. (1999). Fisher discriminant analysis with kernels. Neural Networks for Signal Processing IX, 1999. Proceedings of the 1999 IEEE Signal Processing Society Workshop.

Mika, S., G. Ratsch, et al. (2003). "Constructing descriptive and discriminative nonlinear features: Rayleigh coefficients in kernel feature spaces." Pattern Analysis and Machine Intelligence, IEEE Transactions on 25(5): 623-628.

Ye, J., K. Chen, et al. (2008). Heterogeneous Data Fusion for Alzheimer's Disease Study. Proceedings of the 14th ACM SIGKDD International Conference on Knowledge Discovery and Data Mining. Las Vegas, Nevada, USA, ACM: 1025-1033.

Ye, J., S. Ji, et al. (2008). "Multi-class Discriminant Kernel Learning via Convex Programming." J. Mach. Learn. Res. 9: 719-758.

Zien, A., C.S. Ong, (2007). "Multiclass Multiple Kernel Learning." Proceedings of the 24th International Conference on Machine Learning. Corvallis, OR, USA.

Gonen, M., E. Alpaydm (2011). "Multiple Kernel Learning Algorithms." Journal of Machine Learning Research. 12: 2211-2268.

Shawne-Taylor, J. and N. Cristianini (2004). "Properties of Kernels," Kernel Methods for Pattern Analysis, Cambridge University Press, pp. 47-59.

* cited by examiner

METHOD FOR INTEGRATING AND FUSING HETEROGENEOUS DATA TYPES TO PERFORM PREDICTIVE ANALYSIS

CROSS-REFERENCE TO RELATED APPLICATIONS

This application claims priority under 35 U.S.C. § 119 from provisional application Ser. No. 61/765,530, filed on Feb. 15, 2013, which is incorporated by reference herein in its entirety.

FEDERALLY SPONSORED RESEARCH

This invention was made with government support under Contract No. W81XWH-10-1-0785 awarded by the U.S. Army. The U.S. Government has certain rights in this invention.

BACKGROUND

Technical Field

The technical field relates generally to classification and prediction algorithms for use with a dataset composed of information from heterogeneous data types.

Background Discussion

Kernel methods are a class of algorithms used for pattern analysis. Kernel methods can be used to map input data into a high dimensional or infinite dimensional inner-product, or Hilbert feature space, where each dimension corresponds to a feature. In the feature space, a variety of methods may be used to find relationships within the input data.

SUMMARY

One or more aspects of the present disclosure involve embodiments directed to a disease prediction system for predicting the onset of a disease. The system can comprise a memory storing a training data set including a first plurality of training samples of a first data type and a corresponding second plurality of training samples of a second data type, the first data type including discrete data and the second data type including continuous data, one or more processors coupled to the memory, a disease prediction component executable by the one or more processors and configured to: receive patient data including a first input sample of the first data type and a second input sample of the second data type, provide the first input sample and the first plurality of training samples to a first kernel function of a multiple kernel decision function, provide the second input sample and the second plurality of training samples to a second kernel function of the multiple kernel decision function, perform at least one calculation using the multiple kernel decision function to produce at least one result, and determine a probability of whether the patient data indicates that the patient will develop the disease based on the at least one result of the multiple kernel decision function.

In accordance with some embodiments, the disease prediction component is further configured to perform the at least one calculation using the multiple kernel function at least in part by calculating at least one of a first set of weighting factors and a second set of weighting factors, the first set of weighting factors including a weight for each training sample in the training data set, the second set of weighting factors including a weight for each data type.

In accordance with some embodiments, the disease prediction system is for predicting the onset of Alzheimer's disease in individuals who express mild cognitive impairment.

One or more further aspects of the present disclosure involve embodiments directed to a method for predicting the onset of a disease. The method can comprise receiving patient data including a first input sample of a first data type and a second input sample of a second data type, the first data type including discrete data and the second data type including continuous data, receiving a training data set including a first plurality of training samples of the first data type and a corresponding second plurality of training samples of the second data type, providing the first input sample and the first plurality of training samples to a first kernel function of a multiple kernel decision function, providing the second input sample and the second plurality of training samples to a second kernel function of the multiple kernel decision function, performing at least one calculation using the multiple kernel decision function to produce at least one result, and determining a probability of whether the patient data indicates that the patient will develop the disease based on the at least one result of the multiple kernel decision function.

In accordance with some embodiments, performing the at least one calculation using the multiple kernel function includes calculating at least one of a first set of weighting factors and a second set of weighting factors, the first set of weighting factors including a weight for each training sample in the training data set, the second set of weighting factors including a weight for each data type.

One or more further aspects of the present disclosure are directed to a method for predicting the probability of an event comprising receiving a plurality of input samples, each input sample of the plurality of input samples having a data type of a plurality of data types, the data types including quantitative data, discrete data, continuous data, and categorical data, receiving a training data set including a plurality of training samples, each of the plurality of training samples having a data type of the plurality of data types, providing each input sample and each respective training sample with the same data type of the plurality of training samples to a corresponding kernel function of a multiple kernel decision function having a plurality of kernel functions, performing at least one calculation using the multiple kernel decision function to produce at least one result, and determining a probability of an event based on the at least one result of the multiple kernel decision function.

In accordance with some embodiments, at least one of the first kernel function and the second kernel function is a radial basis function.

In accordance with some embodiments, the multiple kernel decision function is consistent with a Kernel Fisher Discriminant Analysis classifier.

In accordance with some embodiments, the multiple kernel decision function is consistent with a Support Vector Machine classifier.

In accordance with some embodiments, the discrete data includes results from at least one cognitive assessment exam and the continuous data includes results from at least one rate of glucose uptake by tissue.

In accordance with some embodiments, the at least one cognitive assessment exam is selected from the list consisting of: an Alzheimer's Disease Assessment Score, a Mini Mental State Exam, a Boston Naming Test, and an American National Adult Reading Test.

In accordance with some embodiments, the at least one rate of glucose uptake by tissue is retrieved from one or more voxels of the brain selected from the list consisting of: left angular gyrus, right angular gyrus, left temporal, right temporal, and bilateral cingulum posterior.

Still other aspects, embodiments, and advantages of these example aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed aspects and embodiments. Embodiments disclosed herein may be combined with other embodiments, and references to "an embodiment," "an example," "some embodiments," "some examples," "an alternate embodiment," "various embodiments," "one embodiment," "at least one embodiment," "this and other embodiments" or the like are not necessarily mutually exclusive and are intended to indicate that a particular feature, structure, or characteristic described may be included in at least one embodiment. The appearances of such terms herein are not necessarily all referring to the same embodiment.

BRIEF DESCRIPTION OF DRAWINGS

Various aspects of at least one embodiment are discussed below with reference to the accompanying figures, which are not intended to be drawn to scale. The figures are included to provide an illustration and a further understanding of the various aspects and embodiments, and are incorporated in and constitute a part of this specification, but are not intended as a definition of the limits of any particular embodiment. The drawings, together with the remainder of the specification, serve to explain principles and operations of the described and claimed aspects and embodiments. For purposes of clarity, not every component may be labeled in every figure. In the figures:

DETAILED DESCRIPTION

Figure 1:
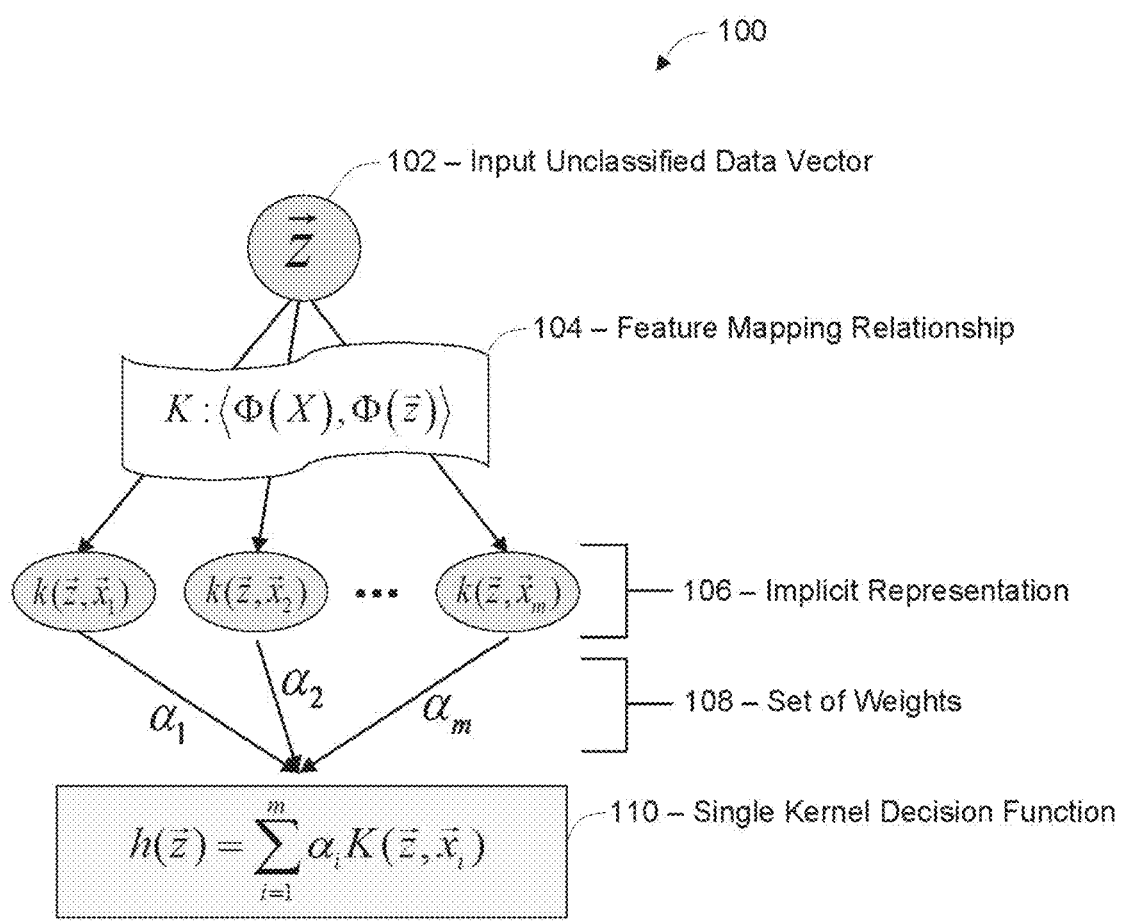
FIG. 1 is a diagram of a single kernel classification algorithm in accordance with one example.

By way of introduction, aspects of this disclosure relate to systems and methods for predicting the probability of an event using a multiple kernel decision function. The method may include receiving a plurality of input samples, where each input sample corresponds to a data type. The data types may include quantitative data, discrete data, continuous data, and categorical data. The method may further include receiving a training data set that includes a plurality of training samples, where each of the plurality of training samples corresponds to a data type. Each input sample and each respective training sample with the same data type of the plurality of training samples may correspond to a kernel function of a multiple kernel decision function having a plurality of kernel functions. At least one calculation may be performed using the multiple kernel decision function to produce at least one result, and the probability of the event may be determined based on the at least one result.

The aspects disclosed herein in accordance with the present invention are not limited in their application to the details of construction and the arrangement of components set forth in the following description or illustrated in the accompanying drawings. These aspects are capable of assuming other embodiments and of being practiced or of being carried out in various ways. Examples of specific implementations are provided herein for illustrative purposes only and are not intended to be limiting. In particular, acts, components, elements, and features discussed in connection with any one or more embodiments are not intended to be excluded from a similar role in any other embodiments.

Also, the phraseology and terminology used herein is for the purpose of description and should not be regarded as limiting. Any references to examples, embodiments, components, elements or acts of the systems and methods herein referred to in the singular may also embrace embodiments including a plurality, and any references in plural to any embodiment, component, element or act herein may also embrace embodiments including only a singularity. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. In addition, in the event of inconsistent usages of terms between this document and documents incorporated herein by reference, the term usage in the incorporated reference is supplementary to that of this document; for irreconcilable inconsistencies, the term usage in this document controls. Moreover, titles or subtitles may be used in the specification for the convenience of a reader, which shall have no influence on the scope of the present invention.

In accordance with certain aspects, classification and prediction algorithms may be optimized for use with one or more datasets comprising information from a wide range of disparate sources. Such heterogeneous data sets may contain a mixture of different types of quantitative, discrete, continuous, and categorical data, and may further include one or more signals collected from multiple sensors sampled at different time scales. The predictive and diagnostic algorithms built from these kinds of datasets may be referred to as heterogeneous data fusion algorithms. These algorithms are capable of being optimized to exploit both the unique and complementary information each type of data provides.

MKL Algorithm Overview

According to one example, a type of heterogeneous data fusion algorithm includes a Multiple Kernel Learning (MKL) classification algorithm, also referred to as a multiple kernel decision function, for purposes of predicting and diagnosing. For example, the MKL algorithm may be used to predict or determine the probability of an event based on training data and sample data constructed from sets of heterogeneous data types of data. According to another aspect, the MKL algorithm may be used for diagnostic purposes, such as for diagnostic patients suffering from one or more symptoms or possessing certain characteristics. The methodology is an expansion of single-kernel machine learning classification algorithms that may be used to develop "class" or "group" discriminating functions. Given a set of data points describing the characteristics of several distinct groups, a classification algorithm will learn a mathematical "rule" for separating the groups. A kernel-based classifier first transforms the data from raw data space into a higher dimensional space, where it may be more linearly separable. Through optimization, a decision function may be identified that separates the classes or groups in the new "feature" space. New unlabeled data points may then be classified based on where they are positioned relative to the hyperplane.

Applications for MKL

The MKL approach creates a method for creating and maximizing diagnostic and predictive power from sets of heterogeneous data. The underlying premise is that using one or more combinations of different data types allows for greater diagnostic and predictive capability than by considering each data type in isolation. This type of analysis is useful in problems where many different types of data are involved. For example, the different types of data may include quantitative data, discrete data, continuous data, and categorical data. Statistically, discrete data may result from either a finite or a countable infinity of possible options for the values present in a given discrete data set. Therefore, discrete data may represent data that can only take certain values, and may be a count of something. Further, discrete data may include numerical, ordinal, or qualitative (nominal) kinds of data. In contrast, continuous data may be measured, and may be capable of taking any numerical value. The numerical values may be subdivided into finer increments, depending upon the desired precision. Quantitative data may refer to measurable data, and may include discrete or continuous types of data. Categorical data may result from placing individual values into groups or categories. Categorical data may be derived from quantitative or qualitative types of data.

An example of an area where the MKL approach may be useful is the medical field, where certain types of diseases or conditions may be the result of very diverse and different types of inputs, including continuous data, such as physical data that may be collected from tests conducted on a patient's body, and discrete data, such as cognitive data that may be collected from tests completed by the patient using their mental capacity. Other types of data may also be included that relates to the patient, such as demographic data, and data related to medical, psychiatric, and family history.

One or more other examples of areas where the MKL approach may be useful may occur in the field of engineering, where predictive algorithms may be useful in determining locations of natural resources, failure points in a structure, weather patterns, and natural disasters such as earthquakes, tornadoes, and tsunamis. Rescue recovery operations, containment exercises (e.g., oil spills), process manufacturing, construction methods, and election prediction are also areas that may benefit from the MKL approach to one or more problems of interest.

An especially useful application for the MKL approach is for predicting whether a population with certain characteristics will develop a certain type of condition and can be diagnosed with a certain type of condition. According to one example, individuals with a history of multiple concussions and other forms of head injury (such as individuals who play football or engage in boxing) may develop Chronic Traumatic Encephalopathy (CTE). According to another example, soldiers returning from war or combat conditions may suffer from at least one of Post-Traumatic Stress Disorder (PTSD) and Mild Traumatic Brain Injury (MTBI). The MKL approach is capable of mathematically "homogenizing" one or more different types of data, weighting them, and then combining their weighted contributions to effectively increase the overall separation of classes. This allows for greater accuracy in predicting and diagnosing these disorders. The functionality is tied to the ability to optimize combinations of different types of data.

According to one embodiment, the MKL algorithm may be applied to the problem of predicting whether an individual exhibiting or expressing Mild Cognitive Impairment (MCI) will progress to be diagnosed with Alzheimer's Disease (AD). According to some examples, one or more subsets of data may be used to successfully predict conversion of MCI to AD using an MKL classification algorithm. For instance, the MKL algorithm may use the combination of discrete data, such as the results from at least one cognitive assessment exam, with continuous data, such as the rate of glucose uptake by tissue (e.g., FDG-PET) to provide a probability that a patient with MCI will develop AD.

Many medical conditions or diseases such as AD may be analyzed using different types of data sources that may include discrete, continuous, quantitative, and categorical data types. For example, results from neuroimaging, psychophysiology, biological assays, psychosocial history, medical history, and gene expression may all be used to form a complete diagnosis. Useful data may include results collected from brain metabolite concentrations derived from Nuclear Magnetic Resonance (NMR) spectroscopy, MRI images, fluorodeoxyglucose-positron emission tomography (FDG-PET) glucose levels, cerebrospinal fluid (CSF) biomarkers, cognitive assessment(s), genetic profile information, and demographic assessments. Although different types of measurements may convey different diagnostic information, all the data may be related or linked to a certain condition, such as the onset of a disease. These heterogeneous sets of data may be integrated to form cross-modal marker identification, which allows for specific diagnostic and treatment prediction.

According to one example, the heterogeneous sets of data may be used to predict the onset of AD. According to another example, the heterogeneous sets of data may be used to diagnose AD. The actual diagnosis of AD may be made by an individual's Primary Care Physician (PCP) using one or more of the previously mentioned types of data. For example, a diagnosis may include medical and family history, psychiatric history, the results from cognitive tests such as the Alzheimer's Disease Assessment Score, physical and neurologic exams, a history of cognitive and behavioral changes, and results from MRI testing that identifies brain changes and may be capable of eliminating other causes of cognitive decline.

The causes of AD are believed to come from many sources, including: the accumulation of the protein beta-amyloid outside the nerve cells, the accumulation of the protein tau inside neurons, family history, and within the nervous system, the inability or failure of information to transfer at the synapse.

One or more risk factors may be associated with AD. These may include family history, which may be the result of genetic and/or environmental factors, the presence or level of Apolipoprotein E-ε4, which is one of three forms of the APOE gene and provides the blueprint for a protein that carries cholesterol in the bloodstream, Mild Cognitive Impairment (MCI), cardiovascular disease, physical/mental inactivity, high fat diets, and head trauma and/or Traumatic Brain Injury (TBI). In at least one example, an MKL approach may be used to determine a probability of whether an individual exhibiting one or more of these risk factors, such as MCI, will develop AD. In another example, an MKL approach may be used to diagnose an individual exhibiting one or more of these risk factors and/or other diagnostic data to determine if they actually have AD.

Kernels

Kernels are functions that provide a mapping between different vector spaces. In certain instances, the key to the kernel-based classification algorithms is their ability to represent the data in a higher dimensional space. When chosen correctly, kernels may perform an implicit dot product between two vectors in the higher dimensional space without actually having to go into that space. Datasets with non-linear class boundaries in raw data space may become linearly separable when they have been transformed appropriately. However, given the high (and potentially infinite) dimensionality, explicitly mapping the data to the feature space may be computationally intensive. Instead, a kernel function may be employed to perform an implicit mapping of the data to the feature space. The kernel function can be defined below as Equation 1:

$$K(\vec{x},\vec{y}) = \langle \Phi(\vec{x}), \Phi(\vec{y}) \rangle = \Phi(\vec{x})^T \Phi(\vec{y}), \quad (1)$$

where x and y are data vectors in the original data space, and $\Phi$ is a function that can embed the data in the higher dimensional feature space. The kernel function is an operation that can be applied to the data vectors that is equivalent to computing their inner product after they have been embedded in the feature space without actually having to map them first. Kernel evaluations can therefore be used in place of every inner product operation required by optimization algorithms designed to identify class boundaries in feature space. When applied to MKL, a different kernel may be chosen for each modality of data. Commonly used kernel functions include those represented below by Equation 2 and Equation 3. Equation 2 describes a linear kernel function which computes the dot product between two data vectors. Equation 3 represents the Gaussian Radial Basis Function, which performs a non-linear mapping of the data into a higher dimensional feature space. The user may choose a at their own discretion, or may perform an optimization to find the best value.

Linear: $K(\vec{x},\vec{y}) = \vec{x}^T\vec{y}$ (2)

Gaussian Radial Basis Function:

$$K(\vec{x},\vec{y}) = \exp\left(\frac{-\|\vec{x}-\vec{y}\|^2}{2\sigma^2}\right) \quad (3)$$

Classifications in Feature Space

Kernel-based classification algorithms differ primarily in their criterion used to optimize the separation of classes in feature space. One such method is the Support Vector Machine (SVM) classifier, which identifies a linear hyperplane that maximizes the margin between the classes in kernel space. Another method is the Kernel Fisher Discriminant Analysis (KFDA), which approaches the optimization by finding a boundary that maximizes the ratio of between-class scatter and within-class scatter in kernel space. Both of these methods scale well to the multiple-kernel case.

Single-Kernel KFDA

According to certain aspects, the goal of KFDA is to learn a decision function from training samples as illustrated in Equation 4 below:

$$h(z) = w^T \phi_K(z) + b, \quad (4)$$

where w is a vector of feature weights, and b is a constant bias term.

Given a two-class classification problem with m training samples, let $\{x_1, \ldots x_{m+}\} \subset \mathbb{R}^n$ represent samples from the positive class, and $\{x_1, \ldots x_{m-}\} \subset \mathbb{R}^n$ denote samples from the negative class, where $m = m_+ + m_-$. For a given kernel function, K, the sets $\{\phi_K(x_i)\}_{i=1}^{m+}$ and $\{\phi_K(x_i)\}_{i=1}^{m-}$ represent the training set in feature space.

Given an unclassified data vector, the value of the output of the decision function corresponds to its class membership, based on a threshold value optimized during training. In one embodiment, the optimization criteria for the separation of classes using KFDA is the maximization of the ratio of the between-class scatter and within-class scatter, where "scatter" is analogous to multi-dimensional "variance." Assessment of the ratio of the between-class scatter and within-class scatter requires computation of the means and covariances of the class data in feature space. The sample means of the positive and negative classes are computed by the equations 5 and 6, respectively, as shown below:

$$\mu_K^+ = \frac{1}{m_+}\sum_{i=1}^{m+} \phi_K(x_i); \quad (5)$$

$$\mu_K^- = \frac{1}{m_-}\sum_{i=1}^{m-} \phi_K(x_i). \quad (6)$$

Sample covariances of the positive and negative classes may be expressed as equations 7 and 8, respectively, as shown below:

$$\sum_{K}^{+} = \frac{1}{m_+}\sum_{i=1}^{m+}(\phi_K(x_i) - \mu_K^+)(\phi_K(x_i) - \mu_K^+)^T; \quad (7)$$

$$\sum_{K}^{-} = \frac{1}{m_-}\sum_{i=1}^{m-}(\phi_K(x_i) - \mu_K^-)(\phi_K(x_i) - \mu_K^-)^T. \quad (8)$$

The scatter-ratio function is defined in terms of these means (i.e., equations 5 and 6) and covariances (i.e., equations 7 and 8). The scatter-ratio maximization equation is shown below in equation 9 in terms of w and the kernel transform K:

$$F_\lambda^*(K) = \max_w F_\lambda(w, K) \quad (9)$$

$$= \frac{[w^T(\mu_K^+ - \mu_K^-)]^2}{w^T(\sum_K^+ + \sum_K^- + \lambda I)w},$$

In equation 9, λ is a small positive regularization parameter and I is the identity matrix. The class-separability optimization function may be reformulated in terms of kernels, where all inner product computations are replaced with their corresponding kernel transforms. The result is shown in Equation 10 below, where w is redefined as:

$$w^* = \sum_{i=1}^{m} \alpha_i^* \phi_K(x_i). \quad (10)$$

As a result, the decision function may be formulated in terms of kernel computations, as shown below in Equation 11:

$$\begin{aligned} h(z) &= w^T \phi_K(z) + b \\ &= \sum_{i=1}^{m} \alpha_i^* \phi_K^T(x_i) \phi_K(z) \\ &= \sum_{i=1}^{m} \alpha_i^* K(x_i, z) \end{aligned} \quad (11)$$

It is appreciated that the optimal weight vector, $\vec{\alpha}^*$, can be solved using one or more analytical methods.

As described above, a decision function can be constructed that determines which class, among one or more classes, an unidentified input vector belongs to given a set of training samples. FIG. 1 is a diagram of a single kernel classification algorithm 100 in accordance with one example that classifies an input unclassified data vector 102. A feature mapping relationship 104 between the input unclassified data vector 102 is implicitly created by representing the input unclassified data vector relative to each training sample of a set of training samples in kernel space. The values of each comparison in kernel space from the implicit representation 106 are weighted and summed consistent with the set of weights 108 in the decision function 110. The output of the decision function may be compared to a pre-determined threshold to identify the class membership of the input unclassified data vector 102.

Scaling Single-Kernel KFDA for Multiple Kernels

The performance of single-kernel classification methods is dependent on the selection of the kernel, and corresponding kernel parameters. Therefore, meaningful results are linked to the ability to choose meaningful input variables. One approach to this problem is to replace the single kernel with a linear combination of multiple kernels. Each kernel may be assigned a weight, and each of these weights may be optimized in a training phase. This may be implemented using a semi-infinite linear programming (SILP) formulation, with the resulting decision function being of the form shown below in Equation 12:

$$\begin{aligned} h(\vec{z}) &= \sum_{i=1}^{m} \alpha_i \sum_{n=1}^{N} \beta_n k_n(\vec{z}_n, \vec{x}_{i,n}) \\ &= \sum_{i=1}^{m} \alpha_i K_c(\vec{z}, \vec{x}_i), \end{aligned} \quad (12)$$

where N is the number of kernels used to create the composite kernel $K_c$, and the N-dimensional vector $\vec{\beta}$ contains the weights on each sub-kernel, determined through the optimization routine. Similar to the single kernel case, a vector of training sample weights, $\vec{\alpha}$, is also specified. In certain embodiments, the expressions shown in Equation 12 may also include a scalar offset.

Application of MKL-KFDA to Heterogeneous Data

Figure 2:
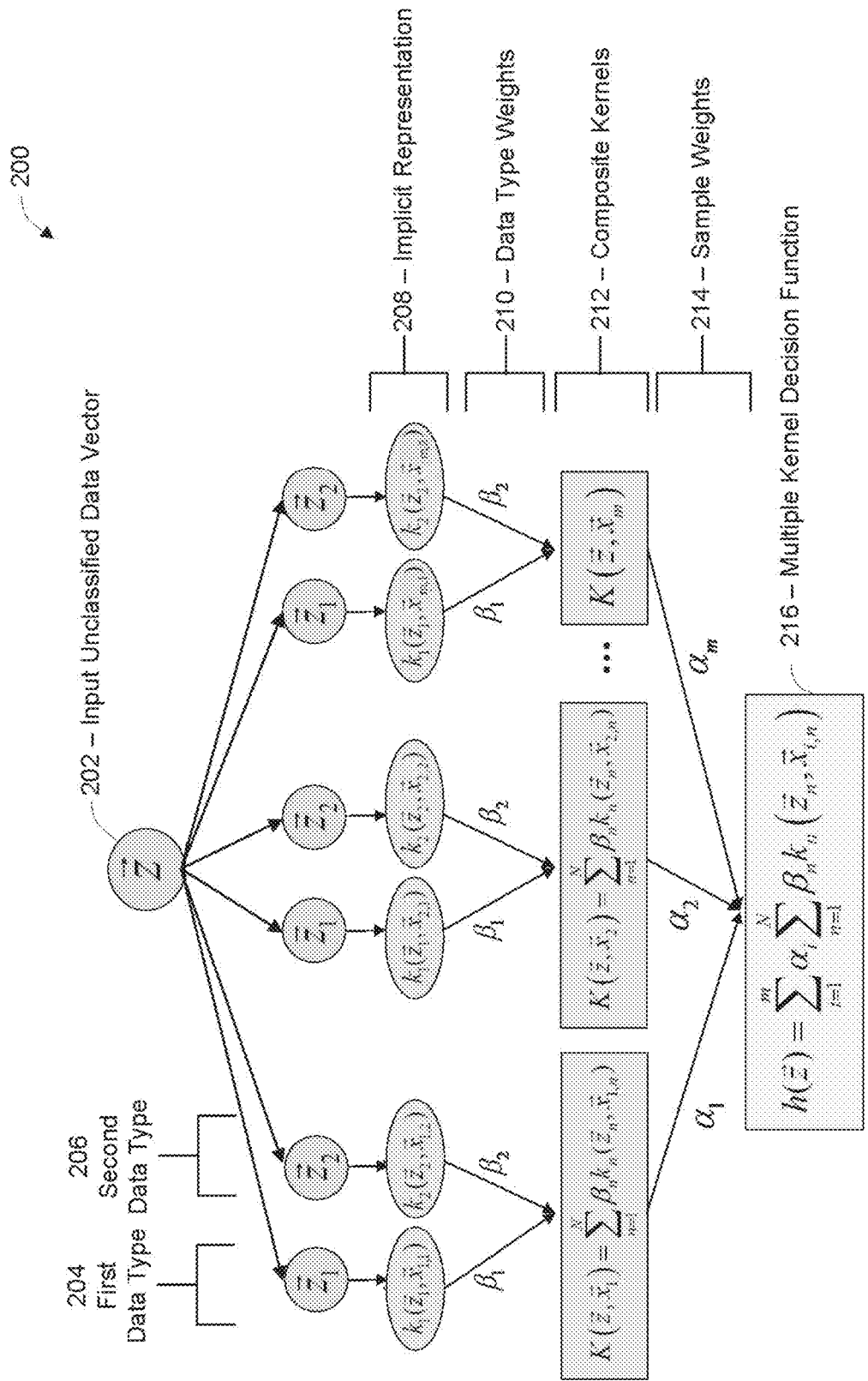
FIG. 2 is a diagram of a multiple kernel classification algorithm in accordance with another example.

Identifying an optimal composite kernel offers a built-in utility for facilitating integration of heterogeneous data from multiple sources. For example, a single kernel may be assigned to each different data type. FIG. 2 is a diagram of a multiple kernel classification algorithm 200 that illustrates how this process may be implemented for a dataset composed of two heterogeneous data types. The input unclassified data vector 202 is a single D-dimensional data vector that can be partitioned as $\vec{z} = [\vec{z}_1 | \vec{z}_2]^T$ where $\vec{z}_1$ is of a first data type 204 and $\vec{z}_2$ is of a second data type 206. The dimensions of $\vec{z}_1$ and $\vec{z}_2$ are $d_1$ and $d_2$, respectively, and $D = d_1 + d_2$. Each data type is transformed into its own kernel space relative to the corresponding data in each training sample as illustrated by implicit representation 208. Composite kernels 212 are formed based on a weighted combination consistent with the data type weights 210. For a given training sample $\vec{x}_i$, the composite kernel $$K_c(\vec{x}_i, \vec{z}) = \sum_{n=1}^{2} \beta_n k_n(\vec{x}_{i,n}, \vec{z}_n)$$

is formed. This process is repeated until the unclassified sample vector has been compared to all m training samples in a similar fashion. Finally, the output of the composite kernels 212 is weighted and summed consistent with a set of samples weights 214 in a multiple kernel decision function 216. The output of the multiple kernel decision function is then employed to determine class membership.

Although the previous discussion used an example with two heterogeneous data types, it is within the scope of this disclosure to include more than two heterogeneous data types. Multiple heterogeneous data types may be considered, as would be appreciated by one of ordinary skill in the art. Further, an SVM approach may be used instead of the KFDA approach used in the example above.

EXAMPLES

An MKL-KFDA algorithm was applied to the problem of predicting whether an individual having Mild Cognitive Impairment (MCI) would progress to having Alzheimer's Disease (AD). The dataset utilized in this test case was collected as part of the Alzheimer's Disease Neuroimaging Initiative (ADNI) project, and was constructed from a diverse array of data collected from hundreds of participants, including demographic data, cognitive exam scores, MRI images and voxel volumes, FDG-PET glucose metabolism levels, and genotypes.

From the diverse array of data collected through the ADNI project, the analysis focused on establishing the utility of participants' FDG-PET glucose metabolism levels in five brain voxels, and four cognitive exam scores collected at baseline as predictors of their conversion from MCI to AD within a four-year period. Table 1 contains the population breakdown of the dataset used in this analysis. All MCI converters were grouped together, regardless of their time-to-conversion from baseline.

TABLE 1

Description of the subject population used in the analysis

| | | | | |
|---|---|---|---|---|
| Number of MCI individuals at baseline | 198 | | | |
| Number of MCI individuals who did not convert to AD | 126 | | | |
| Number of MCI individuals who did convert to AD | 72 | | | |
| Breakdown of converters | Month 6 | Month 12 | Month 24 | Month 48 |
| | 5 | 46 | 18 | 3 |

Table 2 describes the data used in the analysis. The data set combines both discrete (cognitive exams scores) and continuous (FDG-PET) variables, collected from different sources. Four cognitive exam scores (explained further below) and FDG-PET glucose metabolism levels (which is linked to synaptic activity) from five brain voxels were used to create a nine-dimensional feature vector. In the MKL analysis, each set of features was represented by a separate kernel. Therefore, the cognitive exam scores represented one kernel and the FDG-PET results represented a second kernel.

TABLE 2

Description of features used in the analysis

| Kernel | Feature | Description |
|---|---|---|
| 1 | ADAS Score | Alzheimer's Disease Assessment Score - evaluates cognitive impairment in the assessment of Alzheimer's disease |
| | MMSE Score | Mini Mental State Exam - samples functions including arithmetic, memory, and orientation; tests for cognitive impairment |
| | BNT Score | Boston Naming Test - patients with anomic aphasia often have greater difficulties with the naming both difficult and low frequency objects, as well as easy and high frequency objects |
| | ANART Score | American National Adult Reading Test - estimates levels of premorbid intelligence |
| 2 | FDG-PET: Left Angular Gyrus | Glucose metabolism, left angular gyrus voxel |
| | FDG-PET: Right Angular Gyrus | Glucose metabolism, right angular gyrus voxel |
| | FDG-PET: Left Temporal | Glucose metabolism, left temporal voxel |
| | FDG-PET: Right Temporal | Glucose metabolism, right temporal voxel |
| | FDG-PET: Bilateral Cingulum Posterior | Glucose metabolism, bilateral cingulum posterior voxel |

The data compiled from the different tests was analyzed using several methods. To establish the efficacy of the MKL-KFDA technique, a simple Linear Discriminant Analysis (LDA), which is a non-kernel algorithm, was compared against single-kernel SVM and single-kernel KFDA classifiers. The LDA, SVM, and KFDA classifiers were trained using each feature individually. Table 3 below shows the univariate classification results, which reflect the average of 50 iterations of 5-fold cross-validation. In general, the kernel-based methods performed better than the LDA for all features, and the KFDA classifier performed marginally better than the SVM classifier. Overall, the univariate predictors have an average value of between 50 and 60%.

TABLE 3

Univariate classification results

| | Cognitive Scores | | | | FDG-PET Voxel | | | | |
|---|---|---|---|---|---|---|---|---|---|
| | ADAS Score | MMSE Score | BNT Score | ANART Score | L. Ang | R. Ang | L. Temp | R. Temp | Cing. Post |
| Standard Linear Classifiers | 61.8% | 58.1% | 57.4% | 44.1% | 60.2% | 57.5% | 58.1% | 55.3% | 60.7% |
| Single Kernel SVM | 66.3% | 57.4% | 56.6% | 58.0% | 61.7% | 61.2% | 63.2% | 55.9% | 61.9% |
| Single Kernel KFDA | 66.4% | 58.8% | 59.7% | 59.5% | 61.8% | 61.9% | 63.4% | 57.9% | 62.7% |

Figure 3:
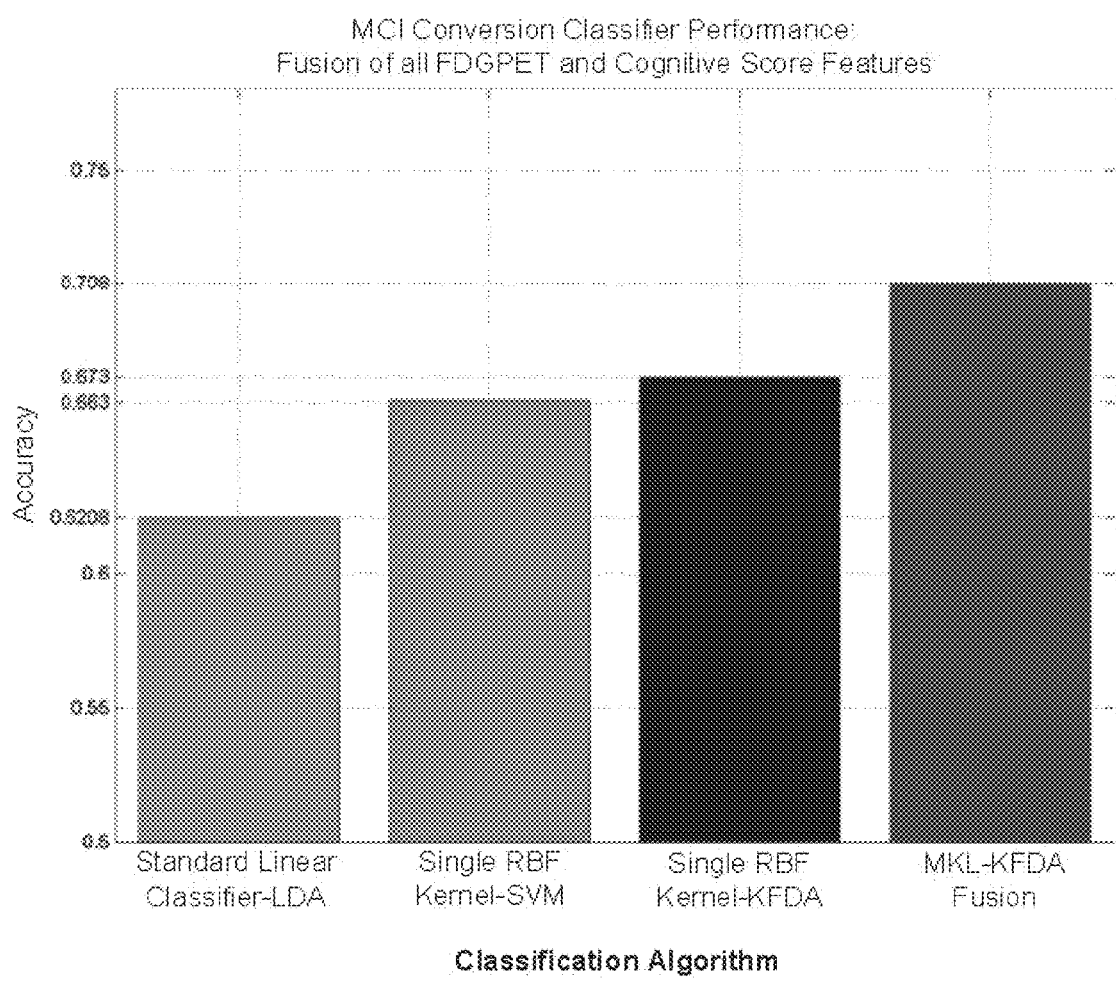
FIG. 3 is a graph illustrating prediction performance using several classification algorithms in accordance with one example.

To further explore the utility of using an MKL algorithm for this type of data, two different kinds of multivariate analysis were performed. In the first approach, an MKL-KFDA method was employed, using two kernels as described above. FIG. 3 shows a graphical comparison of MKL-KFDA against LDA, single kernel SVM, and single kernel KFDA algorithms. All nine features were concatenated into a single vector to train the algorithm. As illustrated in FIG. 3, the MKL-KFDA outperforms the other three types of classifiers.

Figure 4:
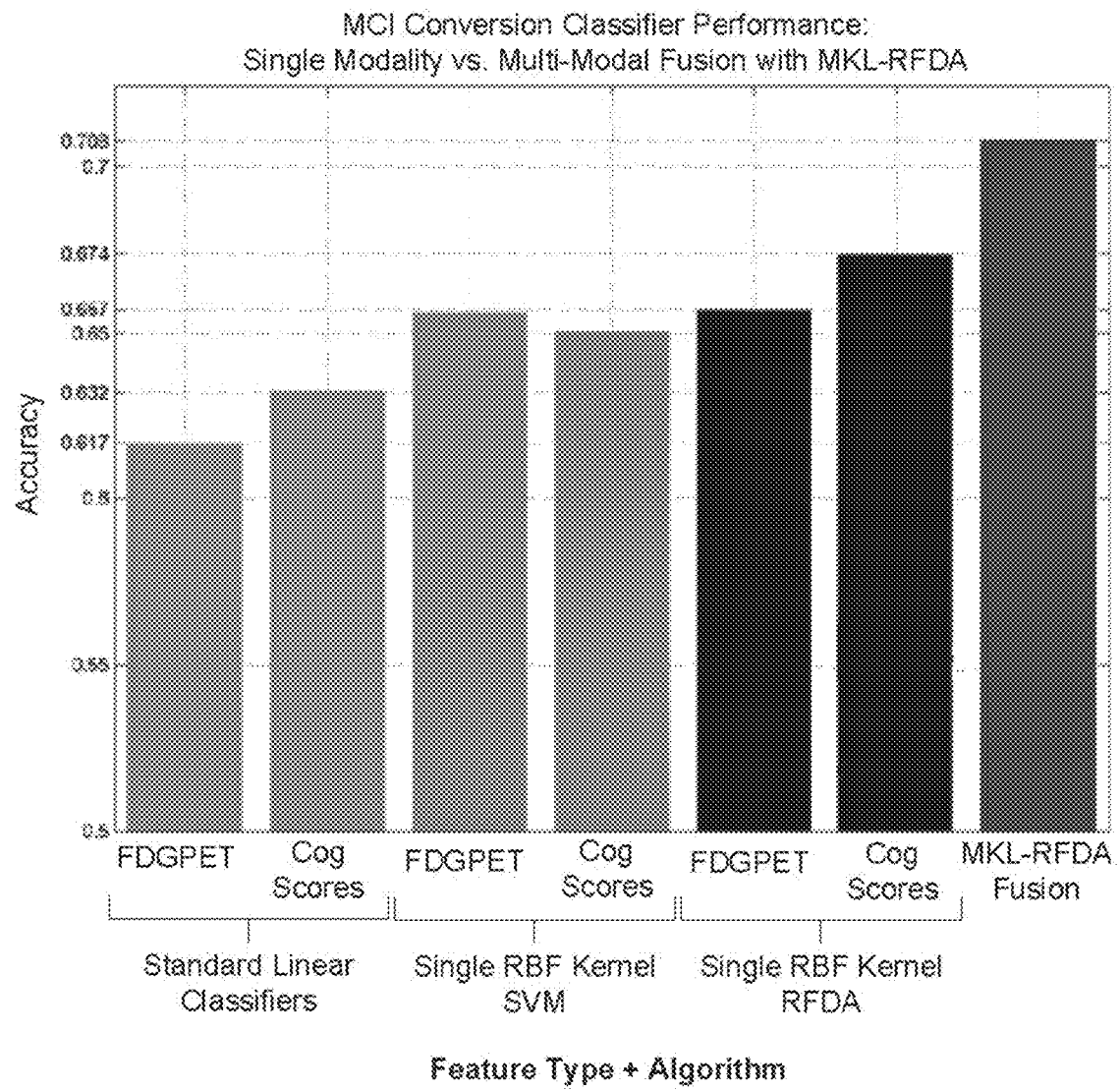
FIG. 4 is a second graph prediction performance using classification algorithms in accordance with another example.

In the second approach, each feature type was used to train each of the LDA, single-kernel SVM, and single-kernel KFDA algorithms. These algorithms were then compared against the MKL-KFDA algorithm. The results of the comparison are shown graphically in FIG. 4. Each feature type offers unique information to the prediction problem, and the MKL method is capable of increasing performance results by using the combination of these features. In other words, the method by which the features are fused determines the strength of their combined efficacy.

A further assessment was conducted on three of the nine different dimensions of data discussed above that exhibited approximately equal balanced percent correct classifications (bPCCs). The bPCC is equivalent to 1-(BER), where BER is the Balanced Error Rate. For example, ADAS is associated with a bPCC value of 65.8%, BNT a value of 60.9%, and FDG-PET with a value of 59.7%. Fusion results in a bPCC value of 72.3%. Table 4 below illustrates the pairwise and three-way agreement when each of these variables is combined with at least one other variable.

TABLE 4

Pairwise and three-way univariate predictor analysis

| Univariate Predictor Variables | % Agree | % Disagree |
|---|---|---|
| ADAS + BNT | 62% | 38% |
| BNT + FDG-PET | 49% | 51% |
| ADAS + FDG-PET | 61% | 39% |
| ADAS + BNT + FDG-PET | 43% | 57% |

Figure 5:
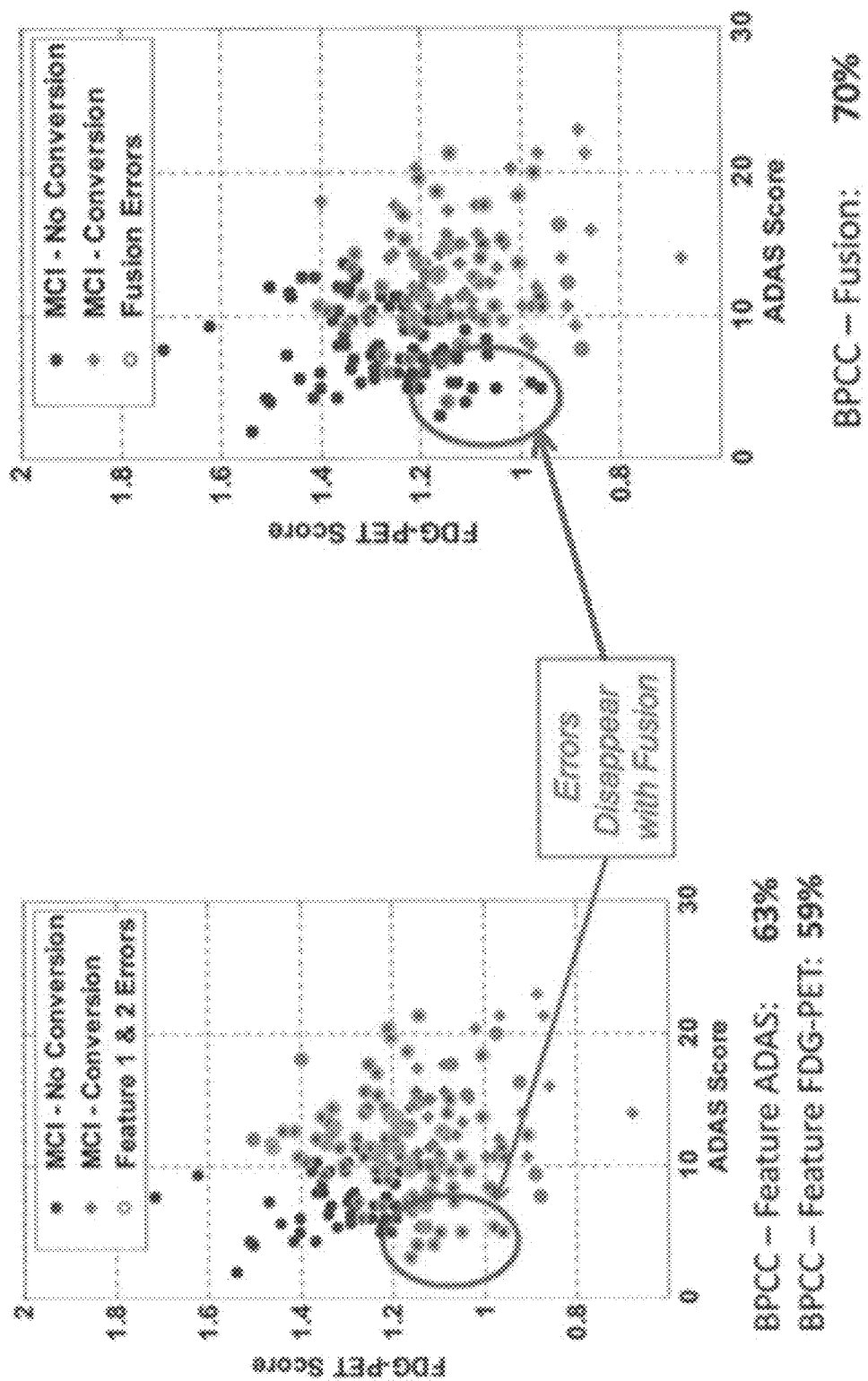
FIG. 5 is a pair of graphs illustrating at least one benefit of using a classification algorithm in accordance with one example.

Referring to Table 4, the "% Agree" refers to the proportion of subjects who were given identical diagnoses by all of the univariate predictor variables. The "% Disagree" refers to the proportion for which the individual predictor variable generated conflicting diagnoses. For example, the ADAS and BNT univariate classification algorithms agreed on the subjects' diagnoses (conversion/non-conversion to AD) 62% of the time. Overall, the results indicate that the pairwise and three-way agreement between the variables is low, which means that similar univariate bPCC values do not necessarily signify similar information. For instance, although the univariate classification accuracies of the BNT and FDG-PET features were similar (~58%), they disagreed in their diagnosis of individuals 51% of the time. This indicates that the BNT scores and FDG-PET are accurate predictors of conversion for different subsets of the subject population, which means they may provide unique, complementary information that may be exploited for better overall diagnostic accuracy. These findings are also exemplified in FIG. 5, where the top graph illustrates the separate bPCC data and resulting error for ADAS and FDG-PET, and the bottom graph illustrates the fusion result of these two data types. This comparison indicates that the error associated with considering the results separately may be reduced when a fusion approach is utilized.

Example Disease Prediction Processes

Figure 6:
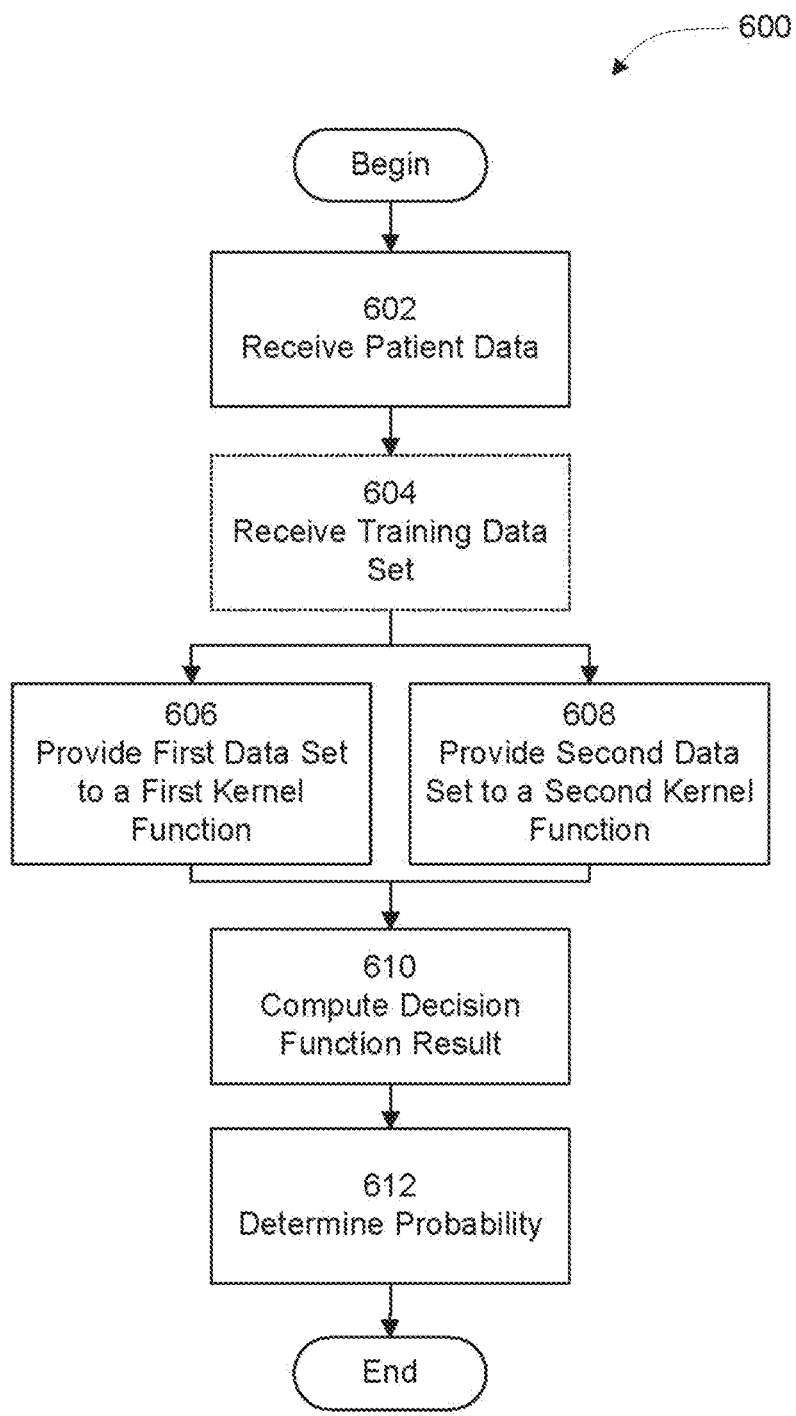
FIG. 6 is a flow diagram of one example method of disease prediction.

As described above with reference to FIGS. 1-5, several embodiments predict the likelihood of predicting a disease. For example, according to one embodiment, the methods and systems disclosed herein may be used to predict the probability that a patient may contract a disease. According to at least one example, the methods and systems disclosed herein may be used to predict the probability that a patient will develop Alzheimer's disease. In some embodiments, the disease prediction processes may be executed by a microprocessor-based computer system, such as the computer system 700 described below with reference to FIG. 7. FIG. 6 illustrates one example disease prediction test process 600 that may be performed by a computer system (e.g., executed by processor 706 of computer system 700). The disease prediction process 600 includes the acts of receiving patient data 602, optionally receiving training data 604, providing first data to a first kernel function 606, providing second data to a second kernel function 608, computing a decision function result 610, and determining a probability 612.

In act 602, the system receives data from a patient. The patient data may include one or more patient samples including one or more data types. For example, the patient samples may include discrete data and continuous data. According to one example, the discrete data may include results from at least one cognitive assessment exam and the continuous data may include at least one rate of glucose uptake by tissue.

In optional act 604, the system receives a training data set. The training data set may include a first plurality of training samples of a first data type and a corresponding second plurality of training samples of a second data type. According to at least one example, the first data type includes discrete data and the second data type includes continuous data. In one example, the discrete data includes results from at least one cognitive assessment exam and the continuous data includes results from at least one rate of glucose uptake by tissue. Although this example includes first and second data types, multiple data types are within the scope of the systems and methods disclosed herein. Further, other types of data may be included in the algorithm, such as results from an MRI, demographic assessment data, and genetic profile data. In other examples, the algorithm may be used without the inclusion of the cognitive assessment exam data and/or the at least one rate of glucose uptake by tissue.

In another embodiment, optional act 604 of receiving the training data set is only performed once and the received training data is stored in memory (e.g., memory device 710 of computer system 700). In this embodiment, option act 604 may not be repeated for subsequent iterations of the disease prediction process 600.

In acts 606 and 608, the system respectively provides a first data set to a first kernel function and a second data set to a second kernel function. Providing the first data set to the first kernel function may include providing patient data and training data of the first type to the first kernel function. Providing the second data set to the second kernel function may include providing patient data and training data of the second type to the second kernel function.

In act 610, the system computes a decision function result. As discussed with reference to FIG. 2, computing the decision function result may include computing one or more composite kernels (e.g., composite kernels 212) consistent with a set of data type weights (e.g., data type weights 210). The computed one or more composite kernels may be combined consistent with a set of sample weights (e.g., sample weights 214) to generate the decision function result.

In act 612, the system determines a probability of getting a disease based on the computed decision function result. Determining the probability of getting a disease may include comparing the decision function result with one or more threshold values. The threshold values may be determined by an individual, such as a researcher or physician, or may be determined by the system. In certain instances, the threshold value may be specific to the application of interest. For example, the threshold value for one disease may be different than another disease.

Although the previous example discusses a disease prediction process, the process may also be applied to a disease diagnostic process. For example, a disease diagnostic process may includes the acts of receiving patient data, optionally receiving training data, providing data to one or more kernel functions, computing a decision function result, and determining a probability, where the probability is linked to diagnosing a patient. Depending on the application and input data, the patient may be diagnosed with a disease or condition.

Furthermore, various aspects and functions described herein in accordance with the present disclosure may be implemented as hardware, software, firmware or any combination thereof. Aspects in accordance with the present disclosure may be implemented within methods, acts, systems, system elements and components using a variety of hardware, software or firmware configurations. Furthermore, aspects in accordance with the present disclosure may be implemented as specially-programmed hardware and/or software.

Example Computer System

Figure 7:
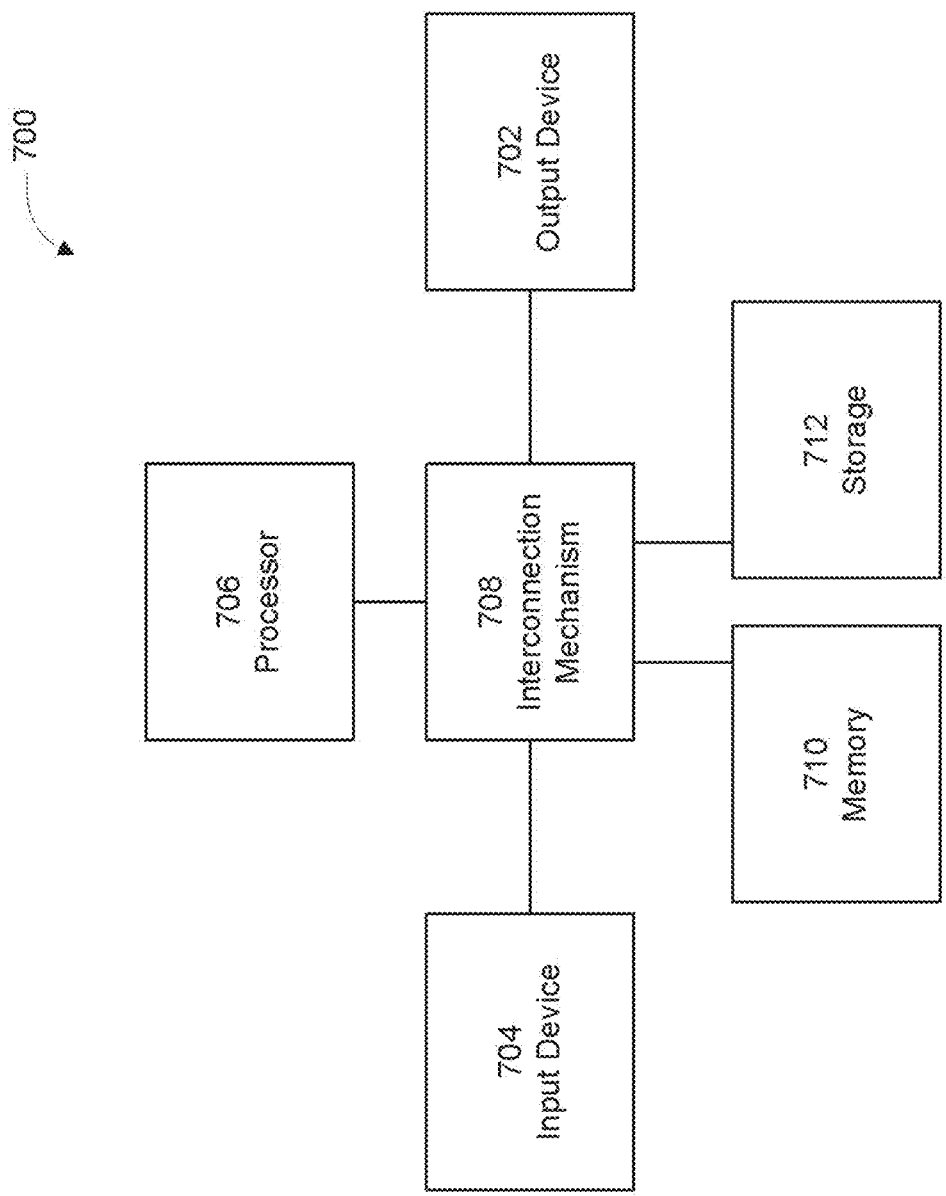
FIG. 7 is a block diagram of one example of a computer system upon which various aspects of the present embodiments may be implemented.

Referring to FIG. 7, there is illustrated a block diagram of one example of computing components forming a system 700 which may be configured to implement one or more aspects disclosed herein. For example, the system 700 may be communicatively coupled to a PCU or included within a PCU and configured to perform an MKL algorithm as described above.

The system 700 may include for example a general-purpose computing platform such as those based on Intel PENTIUM-type processor, Motorola PowerPC, Sun Ultra-SPARC, Texas Instruments-DSP, Hewlett-Packard PA-RISC processors, or any other type of processor. System 700 may include specially-programmed, special-purpose hardware, for example, an application-specific integrated circuit (ASIC). Various aspects of the present disclosure may be implemented as specialized software executing on the system 700 such as that shown in FIG. 7.

The system 700 may include a processor/ASIC 706 connected to one or more memory devices 710, such as a disk drive, memory, flash memory or other device for storing data. Memory 710 may be used for storing programs and data during operation of the system 700. Components of the computer system 700 may be coupled by an interconnection mechanism 708, which may include one or more buses (e.g., between components that are integrated within a same machine) and/or a network (e.g., between components that reside on separate machines). The interconnection mechanism 708 enables communications (e.g., data, instructions) to be exchanged between components of the system 700. Further, in some embodiments the interconnection mechanism 708 may be disconnected during servicing of a PDU.

The system 700 also includes one or more input devices 704, which may include for example, a keyboard or a touch screen. An input device may be used for example to configure the measurement system or to provide input parameters. The system 700 includes one or more output devices 702, which may include for example a display. In addition, the computer system 700 may contain one or more interfaces (not shown) that may connect the computer system 700 to a communication network, in addition or as an alternative to the interconnection mechanism 708.

The system 700 may include a storage system 712, which may include a computer readable and/or writeable nonvolatile medium in which signals may be stored to provide a program to be executed by the processor or to provide information stored on or in the medium to be processed by the program. The medium may, for example, be a disk or flash memory and in some examples may include RAM or other non-volatile memory such as EEPROM. In some embodiments, the processor may cause data to be read from the nonvolatile medium into another memory 710 that allows for faster access to the information by the processor/ASIC than does the medium. This memory 710 may be a volatile, random access memory such as a dynamic random access memory (DRAM) or static memory (SRAM). It may be located in storage system 712 or in memory system 710. The processor 706 may manipulate the data within the integrated circuit memory 710 and then copy the data to the storage 712 after processing is completed. A variety of mechanisms are known for managing data movement between storage 712 and the integrated circuit memory element 710, and the disclosure is not limited thereto. The disclosure is not limited to a particular memory system 710 or a storage system 712.

The system 700 may include a general-purpose computer platform that is programmable using a high-level computer programming language. The system 700 may also be implemented using specially programmed, special purpose hardware, e.g. an ASIC. The system 700 may include a processor 706, which may be a commercially available processor such as the well-known Pentium class processor available from the Intel Corporation. Many other processors are available. The processor 706 may execute an operating system which may be, for example, a Windows operating system available from the Microsoft Corporation, MAC OS System X available from Apple Computer, the Solaris Operating System available from Sun Microsystems, or UNIX and/or LINUX available from various sources. Many other operating systems may be used.

The processor and operating system together may form a computer platform for which application programs in high-level programming languages may be written. It should be understood that the disclosure is not limited to a particular computer system platform, processor, operating system, or network. Also, it should be apparent to those skilled in the art that the present disclosure is not limited to a specific programming language or computer system. Further, it should be appreciated that other appropriate programming languages and other appropriate computer systems could also be used.

Having thus described several aspects of at least one example, it is to be appreciated that various alterations, modifications, and improvements will readily occur to those skilled in the art. For instance, examples disclosed herein may also be used in other contexts. Such alterations, modifications, and improvements are intended to be part of this disclosure, and are intended to be within the scope of the examples discussed herein. Accordingly, the foregoing description and drawings are by way of example only.

What is claimed is:

1. A disease prediction system for predicting the onset of a disease, the system comprising:
 a memory storing a training data set including a first plurality of training samples of a first data type and a corresponding second plurality of training samples of a second data type, the first data type including discrete data and the second data type including continuous data;
 one or more processors coupled to the memory;
 a disease prediction component executable by the one or more processors and configured to program the processor to:
  receive patient data including a first input sample of the first data type and a second input sample of the second data type;
  provide the first input sample and the first plurality of training samples to a first kernel function of a multiple kernel decision function;
  provide the second input sample and the second plurality of training samples to a second kernel function of the multiple kernel decision function;
  perform at least one calculation using the multiple kernel decision function to produce at least one result, wherein the multiple kernel function is configured to homogenize the first and the second data types, and the at least one calculation includes:

calculating at least one of a first set of weighting factors and a second set of weighting factors, the first set of weighting factors including a weight for each training sample in the training data set, the second set of weighting factors including a weight for each data type, and training the multiple kernel function using the training data set, wherein the first and the second sets of weighting factors are adjusted as part of the training;

determine a probability of whether the patient data indicates that the patient will develop the disease based on the at least one result of the multiple kernel decision function; and present the probability of whether the patient data indicates that the patient will develop the disease on a display.

2. The disease prediction system of claim 1, wherein at least one of the first kernel function and the second kernel function is a radial basis function.

3. The disease prediction system of claim 1, wherein the multiple kernel decision function is consistent with a Kernel Fisher Discriminant Analysis classifier.

4. The disease prediction system of claim 1, wherein the multiple kernel decision function is consistent with a Support Vector Machine classifier.

5. The disease prediction system of claim 1, wherein the disease prediction system is for predicting the onset of Alzheimer's disease in individuals who express mild cognitive impairment.

6. The disease prediction system of claim 5, wherein the discrete data includes results from at least one cognitive assessment exam and the continuous data includes results from at least one rate of glucose uptake by tissue.

7. The disease prediction system of claim 6, wherein the at least one cognitive assessment exam is selected from the list consisting of: an Alzheimer's Disease Assessment Score, a Mini Mental State Exam, a Boston Naming Test, and an American National Adult Reading Test.

8. The disease prediction system of claim 6, wherein the at least one rate of glucose uptake by tissue is retrieved from one or more voxels of the brain selected from the list consisting of: left angular gyrus, right angular gyms, left temporal, right temporal, and bilateral cingulum posterior.

9. A method for predicting the onset of a disease, the method comprising:

receiving patient data including a first input sample of a first data type and a second input sample of a second data type, the first data type including discrete data and the second data type including continuous data;

receiving a training data set including a first plurality of training samples of the first data type and a corresponding second plurality of training samples of the second data type;

providing the first input sample and the first plurality of training samples to a first kernel function of a multiple kernel decision function;

providing the second input sample and the second plurality of training samples to a second kernel function of the multiple kernel decision function;

performing at least one calculation using the multiple kernel decision function to produce at least one result, wherein the multiple kernel function is configured to homogenize the first and the second data types, and the at least one calculation includes:

calculating at least one of a first set of weighting factors and a second set of weighting factors, the first set of weighting factors including a weight for each training sample in the training data set, the second set of weighting factors including a weight for each data type, and training the multiple kernel function using the training data set, wherein the first and the second sets of weighting factors are adjusted as part of the training; and determining a probability of whether the patient data indicates that the patient will develop the disease based on the at least one result of the multiple kernel decision function; and presenting the probability of whether the patient data indicates that the patient will develop the disease on a display.

10. The method of claim 9, wherein at least one of the first kernel function and the second kernel function is a radial basis function.

11. The method of claim 9, wherein the multiple kernel decision function is consistent with a Kernel Fisher Discriminant Analysis classifier.

12. The method of claim 9, wherein the multiple kernel decision function is consistent with a Support Vector Machine classifier.

13. The method of claim 9, wherein the method is used for predicting the onset of Alzheimer's disease in individuals who express mild cognitive impairment.

14. The method of claim 13, wherein the discrete data includes results from at least one cognitive assessment exam and the continuous data includes results from at least one rate of glucose uptake by tissue.

15. The method of claim 14, wherein the at least one cognitive assessment exam is selected from the list consisting of: an Alzheimer's Disease Assessment Score, a Mini Mental State Exam, a Boston Naming Test, and an American National Adult Reading Test.

16. The method of claim 14, wherein the at least one rate of glucose uptake by tissue is retrieved from one or more voxels of the brain selected from the list consisting of: left angular gyrus, right angular gyrus, left temporal, right temporal, and bilateral cingulum posterior.

17. A method for predicting the probability of an event comprising:

receiving a plurality of input samples, each input sample of the plurality of input samples having a data type of a plurality of data types, the data types including quantitative data, discrete data, continuous data, and categorical data, the plurality of input samples having at least two different data types;

receiving a training data set including a plurality of training samples, each of the plurality of training samples having a data type of the plurality of data types, including the at least two different data types;

providing each input sample and each respective training sample with the same data type of the plurality of training samples to a corresponding kernel function of a multiple kernel decision function having a plurality of kernel functions;

performing at least one calculation using the multiple kernel decision function to produce at least one result, wherein the multiple kernel function is configured to homogenize the plurality of data types, and the at least one calculation includes:

calculating at least one of a first set of weighting factors and a second set of weighting factors, the first set of weighting factors including a weight for each training sample in the training data set, the second set of weighting factors including a weight for each data type, and training the multiple kernel function using the training data set, wherein the first and the second sets of weighting factors are adjusted as part of the training;

determining a probability of an event based on the at least one result of the multiple kernel decision function; and presenting the probability of the event on a display.

18. The method of claim 17, wherein the multiple kernel decision function is consistent with a Kernel Fisher Discriminant Analysis classifier.

* * * * *